United States Patent [19]
Terren et al.

[11] Patent Number: 5,922,311
[45] Date of Patent: Jul. 13, 1999

[54] OIL-IN-WATER EMULSION, COMPOSITIONS COMPRISING AN OIL-IN-WATER EMULSION, AND USES THEREOF

[75] Inventors: Nadia Terren; Sophie Favre, both of Chevilly Larue, France

[73] Assignee: L'Oreal, Paris, France

[21] Appl. No.: 08/795,933

[22] Filed: Feb. 5, 1997

[30] Foreign Application Priority Data

Feb. 7, 1996 [FR] France ................................ 96-01514

[51] Int. Cl.⁶ .................................................... A61K 7/42
[52] U.S. Cl. .................. 424/70.12; 424/70.122; 424/59; 424/63; 424/64; 424/69; 424/70.7
[58] Field of Search ............... 424/70.12, 70.122, 424/59, 63, 64, 69, 70.7

[56] References Cited

U.S. PATENT DOCUMENTS

| | | | |
|---|---|---|---|
| 5,280,099 | 1/1994 | Imperante et al. | 528/28 |
| 5,286,830 | 2/1994 | Imperante et al. | 528/28 |
| 5,302,378 | 4/1994 | Crotty et al. | 424/59 |
| 5,382,381 | 1/1995 | Imperante et al. | 252/312 |

FOREIGN PATENT DOCUMENTS

| | | |
|---|---|---|
| A-0 576 189 | 12/1993 | European Pat. Off. |
| WO-A-93 25179 | 12/1993 | WIPO |
| WO-A-94 14822 | 7/1994 | WIPO |

*Primary Examiner*—Margaret W. Glass
*Attorney, Agent, or Firm*—Finnegan, Henderson, Farabow, Garrett & Dunner, L.L.P.

[57] ABSTRACT

A method of decreasing the transfer and/or migration and/or improving the persistence and/or behavior of an emulsion on the skin, by applying to the skin an oil-in-water emulsion containing an aqueous phase, a fatty phase having in it at least one oil selected from volatile oils, poly($C_1$–$C_{20}$) alkylsiloxanes, and their mixtures, and at least one silicone surfactant having at least one anionic group.

46 Claims, No Drawings

OIL-IN-WATER EMULSION, COMPOSITIONS COMPRISING AN OIL-IN-WATER EMULSION, AND USES THEREOF

The present invention relates to the use of a silicone surfactant and of a selected oil in an oil-in-water emulsion, as well as to an emulsion comprising such a combination and to their application in cosmetics, in pharmaceuticals or in hygienics.

Foundation compositions are generally provided in the form of a more or less fluid cream comprising fatty substances, such as oils, and a particulate phase generally composed of fillers and pigments. These compositions, when they are applied on the skin, exhibit, however, the disadvantage of transferring, i.e., of being deposited, at least partly, while leaving a mark, on certain substrates with which they may be placed in contact and in particular clothing or the skin. This results in a mediocre persistence of the film on the skin, making it necessary to regularly renew the application of the foundation composition. Another disadvantage of the compositions of the prior art lies in the problem of migration of these compositions, i.e., in the fact that the composition has a tendency to spread into the folds and/or wrinkles of the face, creating an unaesthetic effect.

The aim of the present invention is to overcome these disadvantages and the invention provides an emulsion which behaves very well and which exhibits good persistence on the skin.

The inventors have discovered, surprisingly and unexpectedly, that by using a specific silicone surfactant, in combination with a choice of specific oils, it is possible to obtain an oil-in-water emulsion exhibiting the said characteristics and which also exhibits the advantage of not transferring.

More precisely, the invention relates to the use of the combination of a silicone surfactant comprising at least one anionic group and of a fatty phase comprising at least a first oil selected from volatile oils, from poly($C_1$–$C_{20}$)alkyl-siloxanes and from their mixtures in an oil-in-water emulsion in order to decrease the transfer and/or the migration and/or in order to improve the persistence and/or the behavior of the emulsion, or of a composition comprising it, on the skin.

Another subject of the invention relates to the use of the combination of a silicone surfactant comprising at least one anionic group and of a fatty phase comprising at least a first oil selected from volatile oils, from poly($C_1$–$C_{20}$)alkyl-siloxanes and from their mixtures in an oil-in-water emulsion which decreases the transfer and/or which does not migrate on the skin.

Another subject of the invention consists of an oil-in-water emulsion comprising:

(a) an aqueous phase,
(b) a fatty phase comprising at least one first oil selected from volatile oils, from poly($C_1$–$C_{20}$)alkyl-siloxanes and from their mixtures at a content of at least 65% by weight with respect to the total weight of the fatty phase,
(c) a silicone surfactant comprising at least one anionic group selected from the surfactants defined above, with the proviso that, when the silicone surfactant is of formula (I), the fatty phase of the emulsion comprises another fatty substance, other than the said first oil, at a content of less than or equal to 7% by weight with respect to the total weight of the emulsion.

Another subject of the invention relates to a composition, in particular a cosmetic, pharmaceutical or hygienic composition, comprising an emulsion as shown below.

The invention also relates to a process for the non-therapeutic treatment of the skin and/or of the scalp, wherein an emulsion and/or a composition as defined above is/are applied on the skin and/or on the scalp. The invention also relates to a process for making up the skin and/or the scalp, wherein an emulsion and/or a composition as defined above is/are applied on the skin and/or on the scalp.

Preferably, in the above inventive uses, the content of the first oil in the fatty phase of the emulsion is at least 65% by weight with respect to the total weight of the fatty phase.

It has also been found that the emulsion used according to the invention is applied and is spread easily in a homogeneous way, without leaving a greasy feel, and exhibits good cosmetic properties. The film obtained also exhibits a light texture and remains comfortable to wear throughout the day.

Moreover, the emulsion applied on the skin has the advantage of not migrating into the folds of the skin and/or the wrinkles of the face.

Moreover, it is possible to add other additives, such as oils and/or powders (pigments and/or fillers), to the emulsion according to the invention, while retaining a stable emulsion. The emulsion is thus compatible with a large number of cosmetic adjuvants.

Finally, it has been found that the viscosity of the emulsion is stable with time.

The emulsion used according to the invention thus comprises a silicone surfactant which comprises at least one anionic group. The surfactant can thus be an amphoteric surfactant or, preferably, an anionic surfactant.

According to the invention, the anionic group present in the silicone surfactant can be selected from phosphate, sulphate, sulphonate and/or carboxylate groups.

Mention may be made, among silicone surfactants containing a phosphate group, of those of following formulae (I) to (IV):

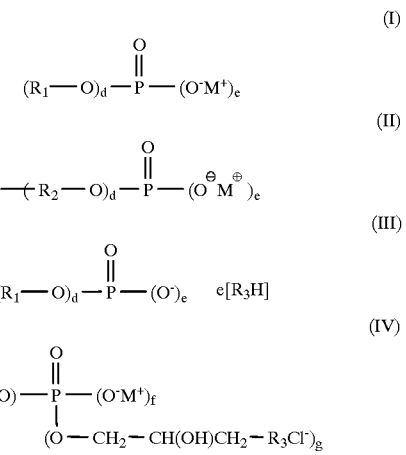

in which formulae:

$R_1$ denotes the radical of following formula (V):

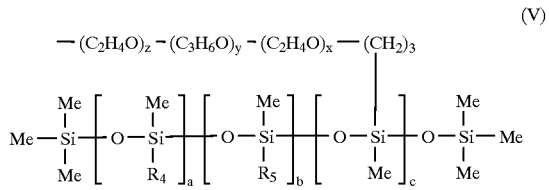

(V)

$R_2$ is the radical of following formula (VI):

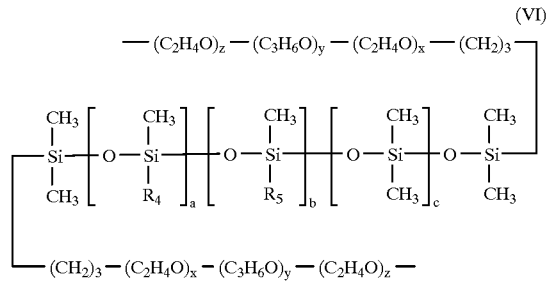

(VI)

in which:

Me denotes a methyl radical, $C_2H_4O$ represents a —$CH_2$—$CH_2$—O— group, $C_3H_6O$ represents a —$CH_2$—$CH(CH_3)$—O— group, a is an integer ranging from 0 to 200, b is an integer ranging from 0 to 200, c is an integer ranging from 1 to 200, $R_4$ denotes a —$(CH_2)_n CH_3$ or phenyl radical, n being an integer ranging from 0 to 10, and $R_4$ preferably denotes a methyl radical, $R_5$ is a —$(CH_2)_3$—$(OCH_2CH_2)_x$—$(OCH_2CH(CH_3))_y$—$(OCH_2CH_2)_z$—OH radical, x, y and z are integers independently ranging from 0 to 20, and preferably $x+y+z \geq 3$, d and e range from 1 to 2, with d+e=3, f is equal to 0 or 1 and g is equal to 1 or 2, with f+g=2, M is selected from the group consisting of H, Na, K, Li, $NH_4$ and $N(CH_2CH_2OH)_3$ $R_3$ is selected from:

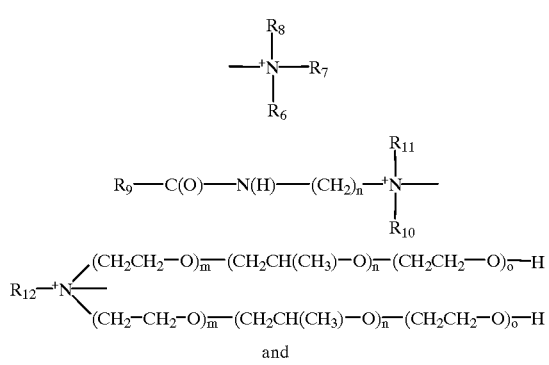

and

-continued

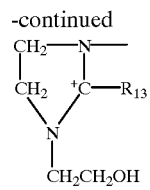

in which formulae:

$R_6$ to $R_9$ independently denote an alkyl radical having from 1 to 20 carbon atoms, $R_{10}$ and $R_{11}$ independently denote an alkyl radical having from 1 to 3 carbon atoms, $R_{12}$ and $R_{13}$ independently denote an alkyl radical having from 6 to 20 carbon atoms, m, n and o independently denote an integer ranging from 0 to 20.

The surfactants of formula (I) are in particular described in U.S. Pat. No. 5,070,171, the disclosure of which is hereby incorporated by reference, and are sold under the names "Pecosil PS-100", "Pecosil PS-200" and "Pecosil WDS-100" by the company Phoenix Chemical. The surfactants of formulae (II), (III) and (IV) are in particular described respectively in U.S. Pat. Nos. 5,149,765, 5,093,452 and 5,091,493, the disclosures of which are hereby incorporated by reference.

Use is preferably made, among silicone surfactants containing a phosphate group, of those of formula (I).

Mention may be made, among silicone surfactants containing a sulphate group, of those of following formula (VII):

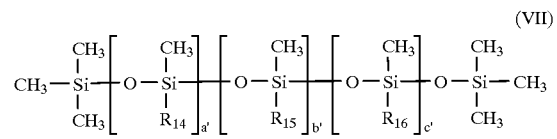

(VII)

in which $R_{14}$ denotes an alkyl radical having from 1 to 8 carbon atoms or a phenyl radical, $R_{15}$ denotes a —$(CH_2)_3$—O—$(CH_2CH_2O)_u$—$(CH_2CH(CH_3)$—O$)_v$—$(CH_2CH_2O)_w$—$SO_3^- M^+$ radical, M being selected from Na, K, Li and $NH_4$, $R_{16}$ denotes a —$(CH_2)_3$—O—$(CH_2CH_2O)_u$—$(CH_2CH(CH_3)$—O$)_v$—$(CH_2CH_2O)_w$—H radical, in which radicals u, v and w independently denote an integer ranging from 0 to 100, a' and c' independently denote an integer ranging from 0 to 50, b' denotes an integer ranging from 1 to 50, and preferably c'=0.

The compounds of formula (VII) are in particular described in U.S. Pat. No. 4,960,845, the disclosure of which is hereby incorporated by reference.

Mention may be made, among silicone surfactants containing a sulphonate group, of those obtained by the reaction of a silicone of formula (VIII):

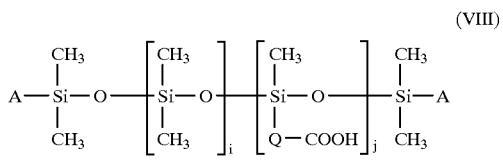

(VIII)

in which

Q denotes $(CH_2)_r$, r being an integer ranging from 3 to 17, j denotes either an integer ranging from 1 to 10 and A denotes a methyl radical or j=0 and A denotes a —Q—COOH radical, I denotes an integer ranging from 1 to 200, with a taurine derivative of formula $R_{17}$—NH—$(CH_2)_2$—$SO_3M$, in which $R_{17}$ denotes an alkyl radical having from 1 to 40 carbon atoms, and M is selected from Na, K, Li and $NH_4$.

The compounds thus prepared are described in U.S. Pat. No. 5,286,830, the disclosure of which is hereby incorporated by reference.

Mention may also be made, as silicone surfactants containing a sulphonate group, of those of following formula (IX):

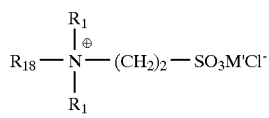

(IX)

in which $R_{18}$ denotes an alkyl radical having from 1 to 40 carbon atoms, $R_1$ denotes a radical of formula (V) as defined above, M' is selected from Na, K, Li and $NH_4$.

The compounds of formula (IX) are in particular described in U.S. Pat. No. 5,280,099, the disclosure of which is hereby incorporated by reference.

Use is preferably made of silicone surfactants comprising at least one phosphate or sulphate group and more preferentially of those containing phosphate groups, in particular surfactants of formula (I).

The emulsion used according to the invention also comprises, in a fatty phase, at least one first oil selected from volatile oils, from poly($C_1$–$C_{20}$)alkyl-siloxanes and from their mixtures at a content of at least 65% by weight with respect to the total weight of the fatty phase.

Volatile oil is understood to mean, in the present description, any oil capable of evaporating on contact with the skin. Use is preferably made of oils which have a flash point which is sufficiently high to enable these oils to be used in formulation and which is sufficiently low to obtain the desired evanescent effect. Oils with a flash point of the order of 40–100° C. and/or with a vapor pressure, measured at $10^5$ Pa and at 25° C., of greater than or equal to 0.02 mm Hg (2.6 Pa) and/or with a boiling point, measured at $10^5$ Pa, of less than or equal to 275° C. are preferably employed.

The volatile oil present in the fatty phase can be selected from volatile hydrocarbon oils, volatile silicone oils and their mixtures.

Mention may be made, among volatile hydrocarbon oils, of isoparaffins and in particular of isododecane.

Mention may be made, among volatile silicone oils, of:

(I) volatile cyclic silicones having from 3 to 8 silicon atoms and preferably from 4 to 6. It relates, for example, to cyclotetradimethylsiloxane, cyclopentadimethylsiloxane or cyclohexadimethylsiloxane, (ii) cyclocopolymers of the dimethylsiloxane/methylalkylsiloxane type, such as Silicone FZ 3109 sold by the company Union Carbide, which is a dimethylsiloxane/methyloctylsiloxane cyclocopolymer, (iii) volatile linear silicones having from 2 to 9 silicon atoms. It relates, for example, to hexamethyldisiloxane, hexylheptamethyltrisiloxane or octylheptamethyltrisiloxane.

The polyalkylsiloxanes according to the invention contain trimethylsilyl end groups. Use may preferably be made of those with a viscosity of 25° C. of less than or equal to 0.06 $m^2$/s, among which may be mentioned:

linear polydimethylsiloxanes and in particular those sold under the names "Dow Corning Fluid 200" by the company Dow Corning alkylmethylpolysiloxanes, such as cetyidimethicone (CTFA name).

The fatty phase preferably comprises at least 75% by weight, with respect to the total weight of the said fatty phase, of oil selected from volatile silicone and/or hydrocarbon oils, from polyalkylsiloxanes and from their mixtures. The said fatty phase of the emulsion advantageously comprises 100% by weight, with respect to the total weight of the fatty phase, of volatile oils, of polydimethylsiloxanes or of their mixtures.

The fatty phase of the emulsion according to the invention can comprise, in addition to the first oils mentioned above, other non-volatile fatty substances commonly used in the envisaged field of application. The fatty phase preferably comprises from 65% to 98% by weight, preferably from 75% to 98%, with respect to the total weight of the fatty phase, of oil selected from volatile silicone and/or hydrocarbon oils, from polyalkylsiloxanes and from their mixtures and from 2% to 35%, preferably from 2% to 25%, by weight of the said other fatty substance.

Mention may be made, among the other fatty substances, of vegetable, mineral, animal and/or synthetic oils, pasty fatty substances, gums and waxes, the synthetic group comprising silicone fatty substances.

Pasty fatty compounds may be defined using at least one of the following physicochemical properties:

a viscosity of 0.1 to 40 Pa·s (1 to 400 poises), preferably 0.5 to 25 Pa·s, measured at 40° C. with a Contraves TV rotary viscometer equipped with an MS-r3 or MS-r4 rotor at a speed of 60 Hz, a melting point of 25–70° C., preferably 25–55° C.

Mention may be made, among silicone fatty substances, of phenylated silicone oils as well as silicone gums and silicone waxes.

Mention may be made, among non-silicone fatty substances, of liquid paraffin, liquid petrolatum, perhydrosqualene, apricot oil, wheat germ oil, sweet almond oil, calophyllum oil, palm oil, castor oil, avocado oil, jojoba oil, olive oil or cereal germ oil; fatty acid esters; alcohols; acetylglycerides; octanoates, decanoates or ricinoleates of alcohols or of polyalcohols; fatty acid triglycerides; glycerides; hydrogenated oils which are solid at 25° C.; lanolins; fatty esters which are solid at 25° C.; beeswax; vegetable waxes, such as carnauba wax, candelilla wax, ouricury wax, Japan wax or cork fibre or sugarcane waxes; mineral waxes, for example paraffin wax, lignite wax or microcrystalline waxes or ozokerites; or synthetic waxes, including polyethylene waxes and the waxes obtained by the Fischer-Tropsch synthesis.

The silicone gums can correspond to the formula:

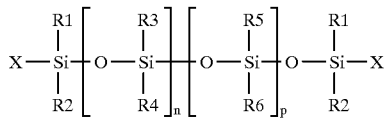

in which:
- R1, R2, R5 and R6 are, together or separately radical having 1 to 6 carbon atoms,
- R3 and R4 are, together or separtely, an alkyl radical having from 1 to 6 carbon atoms or an aryl, and in particular phenyl, radical,
- X is an alky radical having from 1 to 6 carbon atoms, a hydroxyl radical or a vinyl radical,
- n and p being selected so asto confer a viscosity greater than 100,000 mPa·s, preferably greater than 500,000 mPa·s, on the silicone gum.

Generally, n and p can have values from 0 to 5000, perferably from 0 to 3000.

Mention may be made, as silicone gum which can be used according to the invention, of those for which:
- R1 to R6 and X substituents represent a methyl group, p=0 and n=2700, such as that sold under the name SE30 by the company General Electric,
- the R1 to R6 and X substituents represent a methyl group, p=0 and n=3200, such as that sold under the name AK 500000 by the company Waker,
- R1 to R6 substituents represent a methyl group, X substituent represents a hydroxyl group, p=0 and n=2700, as a 13% solution in cyclopentasiloxane, such as that sold under the name Q2-1410 by the company Dow Corning,
- the R1 to R6 substituents represent a methyl group, the X substituent represents a hydroxyl group, p=0 and n=2700, as a 13% solution in polydimethylsiloxane, such as that sold under the name Q2-1403 by the company Dow Corning,
- the R1, R2, R5, R6 and X substituents represent a methyl group and the R3 and R4 substituents represent a phenyl group, such that the molecular weight of the compound is 600,000, such as that sold under the names "761" or "Mirsil C-DPDM" by the company Rhône-Poulenc.

Use is preferentially made, as other fatty substance, of silicone gums. These fatty substances can in particular be selected in a way varied by the person skilled in the art in order to prepare a composition having the desired properties, for example with respect to consistency or texture. They are preferably used at a content of less than or equal to 7% by weight with respect to the total weight of the emulsion, in order to retain the advantageous properties of the emulsion used according to the invention.

The aqueous phase of the emulsion according to the invention can comprise water or a floral water, such as cornflower water. In addition, the aqueous phase can comprise from 0% to 14% by weight, with respect to the total weight of the aqueous phase, of a lower $C_2$–$C_6$ monoalcohol and/or of a polyol, such as glycerol, butylene glycol, isoprene glycol or propylene glycol.

Generally, the emulsion according to the invention can comprise from 5% to 40% by weight of fatty phase, preferably from 12% to 30%; from 0.5% to 15% by weight of silicone surfactant containing an anionic group, preferably from 3% to 6%; and from 15% to 94.5% by weight of aqueous phase, preferably from 40% to 70%.

Moreover, the emulsion according to the invention can comprise from 0 to 5% by weight, with respect to the total weight of the emulsion, of at least one coemulsifier which can be selected from oxyethylenated sorbitan monostearate, fatty alcohols, such as stearyl alcohol or cetyl alcohol, or esters of fatty acids and of polyols, such as glyceryl stearate.

In addition, the emulsion according to the invention can comprise one or a number of thickening agents in preferential concentrations ranging from 0 to 6% by weight with respect to the total weight of the emulsion. The thickening agent can be selected from:
- polysaccharide biopolymers, such as xanthan gum, locust bean gum, guar gum, alginates or modified celluloses, such as hydroxyethyl cellulose or methyl cellulose,
- synthetic polymers, such as poly(glyceryl (meth)acrylate)s, such as Hispagel or Lubragel from the companies Hispano Quimica or Gardian, polyvinylpyrrolidone, poly(vinyl alcohol), crosslinked polymers of acrylamide and of ammonium acrylate, such as PAS 5161 or Bozepol C from Hoechst, or crosslinked polymers of acrylamide and of methacryloyloxyethyltrimethylammonium chloride, such as Salcare SC 92 from Allied Colloids,
- magnesium aluminium silicate.

The emulsion according to the invention can also comprise a particulate phase which can comprise pigments and/or pearlescent agents and/or fillers commonly used in cosmetic compositions.

The pigments can be present in the emulsion in the proportion of 0–20% by weight, with respect to the total weight of the emulsion, and preferably in the proportion of 2–15%. They can be white or coloured, inorganic and/or organic. Mention may be made, among inorganic pigments and nanopigments, of titanium, zirconium or cerium dioxides, as well as of zinc, iron or chromium oxides, nanometre-grade titanium oxides, ferric blue, pearlescent agents, such as mica covered with titanium oxide, with iron oxide, with natural pigment or with bismuth oxychloride, and coloured titanium oxide-coated mica. Mention may be made, among organic pigments, of carbon black and barium, strontium, calcium or aluminium lakes.

The fillers, which can be present in the emulsion in the proportion of 0–20% by weight, with respect to the total weight of the emulsion, preferably 0–10%, can be inorganic or synthetic, lamellar or non-lamellar. Mention may be made of talc, mica, silica, kaolin, teflon, starch, natural mother-of-pearl, boron nitride or microspheres, such as Expancel (Nobel Industrie) or polytrap (Dow Corning). Use is preferably made of spherical fillers which have a size of less than 25 $\mu$m, such as polyethylene powders, nylon powders, silicone resin microbeads (Tospearls from Toshiba) or silica microspheres, it being possible for these fillers to contribute to improving the non-transfer properties of the emulsions of the invention.

The emulsion according to the invention can additionally comprise a cosmetically, pharmaceutically or hygienically acceptable medium. It can then comprise any additive commonly used in the cosmetics, pharmaceuticals or hygienics field, such as antioxidants, dyes, fragrances, essential oils, preservatives, cosmetic active principles, moisturizers, vitamins, sphingolipids, artificial tanning compounds, such as DHA, sunscreening agents or fat-soluble polymers, in particular hydrocarbons; such as polybutene or polyalkylenes, polyacrylates and silicone polymers which are compatible with fatty substances. Of course, the person skilled in the art will take care to choose this or these possible additional compounds, and/or their amount, so that the advantageous properties of the composition according to the invention are not, or not substantially, detrimentally affected by the envisaged addition. These additives can be present in the composition in the proportion of 0–10% by weight.

The emulsions according to the invention can be provided in the form of a cosmetic product and in particular in the form of a care product for the body and/or the face and/or the scalp or alternatively of a make-up product, in particular a foundation, a blusher, an eyeshadow, an eyeliner, a mascara or a lipstick.

They can also be provided in the non-coloured form, optionally containing cosmetic active principles. The emulsion according to the invention can be in the form of a cream, of a milk or of a serum which is capable of being used as a care or anti-sun product.

The following examples serve to illustrate the invention without, however, having a limiting nature.

EXAMPLES 1 to 7

Study of the Properties of Persistence of the Emulsions as a Function of the Nature of the Fatty Phase 5 emulsions (foundation) in accordance with the invention (Examples 1 to 5) and 2 emulsions (foundation) not forming part of the invention (Examples 6 and 7) were prepared, each emulsion differing in the nature of the fatty phase.

The emulsions were prepared according to the following compositions:

| | |
|---|---|
| Fatty phase | X g |
| Silicone surfactant containing a phosphate group (Pecosil PS 100 from the company Phoenix) | 5 g |
| Coemulsifier | 2 g |
| Thickening agents | 0.45 g |
| Pigments | 7 g |
| Dispersing agents | 0.96 g |
| Preservatives | 0.6 g |
| Water | q.s. for 100 g |

The constitution of the fatty phase of each emulsion has been reported in Table I. In Table I:

(I) denotes an example according to the invention (NI) denotes an example not forming part of the invention cyclo D6 is cyclohexadimethylsiloxane.

The compositions were prepared in the usual way, by heating the ingredients of the fatty phase, the coemulsifier and a portion of the preservatives to 65° C. The aqueous phase was then prepared by mixing the water, the silicone surfactant and the pigments, dispersed beforehand with the dispersing agents, while heating at 80° C. The fatty phase was then poured into the aqueous phase at 65° C. while stirring using a propeller and then the thickening agents and the remainder of the preservatives were added at 40° C. to the emulsion obtained.

The properties of persistence of these emulsions were then determined. To do this, 0.05 g of each emulsion was applied over an area of 50 cm$^2$ on the forearm and then the composition applied was allowed to dry for 5 minutes. A strip of polyester cloth was then applied to the part of the forearm treated. Then, using a device, the strip was driven with a vertical translational movement, in contact with the treated forearm. The cloth was held taut using a counterweight, thus creating a rubbing action of the cloth during translation. 10 rubbing to-and-fro movements were carried out. The coloured marks which were possibly deposited on the cloth were then graded according to the following grading:

highly stained cloth: grade=0 mark-free cloth: grade=10

A foundation is regarded as showing little transfer when the grading is equal to or greater than 7.5.

The results obtained are reported in Table I.

TABLE I

| EXAMPLES | 1(I) | 2(I) | 3(I) | 4(I) | 5(I) | 6(NI) | 7(NI) |
|---|---|---|---|---|---|---|---|
| Oil O | PDMS with a viscosity of 10$^{-5}$ m$^2$/s | | Cyclohexadimethylsiloxane | Isododecane | | Apricot oil | |
| Content of oil O with respect to the fatty phase | 100% | 25% | 100% | 25% | 25% | 50% | 100% |
| Content of cyclo D6 with respect to the fatty phase | 0% | 75% | 0% | 75% | 75% | 50% | 0% |
| Content of oil O with respect to the emulsion | 20% | 7.5% | 40% | 5% | 5% | 9% | 19% |
| Total weight (X) of the fatty phase in the emulsion | 20 g | 30 g | 40 g | 20 g | 20 g | 18 g | 19 g |
| Non-transfer result | 8 | 8 | 8.5 | 7.5 | 7.5 | 5.5 | 5 |

The results obtained show that the emulsions in which the fatty phase comprised only PDMS or only volatile silicone (Examples 1 and 3) exhibited good persistence properties and did not transfer onto the cloth.

Likewise, the emulsions in which the fatty phase comprised a mixture of volatile silicone oil with a PDMS (Example 2) or with a volatile hydrocarbon oil (Example 4) did not transfer onto the cloth.

In contrast, among the emulsions comprising a mixture of volatile silicone oil and of apricot oil (Examples 5 to 7), only that in which the content of apricot oil is equal to 5% by weight with respect to the total weight of the emulsion (Example 5) exhibits good persistence properties. These examples therefore show that oils other than PDMSs and volatile oils have to be present in the fatty phase of the emulsion at low contents.

EXAMPLE 8

A foundation having the following composition was prepared:

| | |
|---|---|
| Cyclohexadimethylsiloxane | 14 g |
| Sorbitan monostearate oxyethylenated with 20 mol of ethylene oxide | 2 g |
| Pigments | 7 g |
| Dispersing agents | 1 g |
| Thickening agents | 0.5 g |
| Silicone surfactant containing a phosphate group (Pecosil PS100) | 5 g |
| Glycerol | 5 g |
| Preservatives | 0.6 g |
| Sterilized demineralized water | q.s. for 100 g |

The composition was prepared according to the same procedure of Examples 1 to 7. The foundation thus obtained spread easily on the face and exhibited, after application, good behavior and good persistence.

EXAMPLE 9

A foundation having the following composition was prepared:

| | |
|---|---|
| Cyclohexadimethylsiloxane | 15 g |
| Sorbitan monostearate oxyethylenated with 20 mol of ethylene oxide | 2 g |
| Pigments | 7 g |
| Dispersing agents | 1 g |
| Thickening agents | 0.5 g |
| Silicone surfactant containing a sulphate group, sold under the name Water Soluble Suffate by the Company Siltech | 14.8 g |
| Glycerol | 5 g |
| Preservatives | 0.6 g |
| Sterilized demineralized water | q.s. for 100 g |

The composition was prepared according to the same procedure of Examples 1 to 7. A foundation is thus obtained which spread easily on the skin without a feeling of greasiness and did not transfer on contact with a cloth.

EXAMPLE 10

A foundation having the following composition was prepared:

| | |
|---|---|
| Cyclohexadimethylsiloxane | 15 g |
| Polydimethylsiloxane (viscosity $10^{-5}$ m$^2$/s) | 15 g |
| Sorbitan monostearate oxyethylenated with 20 mol of ethylene oxide | 2 g |
| Pigments | 7 g |
| Dispersing agents | 1 g |
| Thickening agents | 0.5 g |
| Silicone surfactant containing a phosphate group (Pecosil PS 100) | 5 g |
| Glycerol | 5 g |
| Preservatives | 0.6 g |
| Sterilized demineralized water | q.s. for 100 g |

The composition was prepared according to the same procedure of Examples 1 to 7. The foundation thus obtained exhibited good cosmetic properties and did not transfer onto a cloth after application on the skin.

EXAMPLE 11

A cream having the following composition was prepared:

| | |
|---|---|
| Cyclohexadimethylsiloxane | 20 g |
| Sorbitan monostearate oxyethylenated with 20 mol of ethylene oxide | 2 g |
| Dispersing agents | 1 g |
| Thickening agents | 0.5 g |
| Silicone surfactant containing a phosphate group (Pecosil PS 100) | 5 g |
| Glycerol | 5 g |
| Preservatives | 0.6 g |
| Sterilized demineralized water | q.s. for 100 g |

The composition was prepared according to the same procedure of Examples 1 to 7. A cream was obtained which spread easily on the skin and which did not transfer onto a cloth applied on the skin.

EXAMPLE 12

The following composition was prepared:

| | |
|---|---|
| Cyclohexadimethylsiloxane | 11 g |
| Mixture of polydiphenyldimethylsiloxane and of cyclopentadimethylsiloxane (15/85) ("Mirasil C-DPDM" from Rhone-Poulenc) | 3 g |
| Thickeners | 1.28 g |
| Nylon powder | 2 g |
| Pigments | 8 g |
| Silicone surfactant containing a phosphate group ("Pecosil PS 100") | 5 g |
| Sorbitan monostearate oxyethylenated with 20 mol of ethylene oxide | 2 g |
| Glycerol | 5 g |
| Preservatives | q.s. |
| Demineralized water | q.s. for 100 g |

The composition was prepared according to the same procedure of Examples 1 to 7. A foundation was obtained which spread easily on the skin and which did not transfer onto a cloth applied on the skin.

We claim:

1. A method of decreasing the transfer and/or migration of or improving the persistence and/or behavior of an emulsion on the skin, said method comprising the step of applying to the skin an oil-in-water emulsion comprising:

at least one silicone surfactant comprising at least one anionic group;

a fatty phase comprising at least one oil selected from volatile oils and poly ($C_{1-C20}$)alkylsiloxanes; and an aqueous phase, said at least one silicone surfactant and said fatty phase being present in the emulsion in an amount sufficient to decrease the transfer and/or migration of or to improve the persistence and/or behavior of said emulsion on the skin.

2. A method according to claim 1, wherein said at least one silicone surfactant is selected from surfactants containing at least one group selected from phosphate, sulphate, sulphonate, or carboxylate.

3. A method according to claim 2, wherein said at least one silicone surfactant contains a phosphate group and is selected from compounds of formula (I):

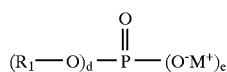

wherein

R₁ represents a radical of formula (V):

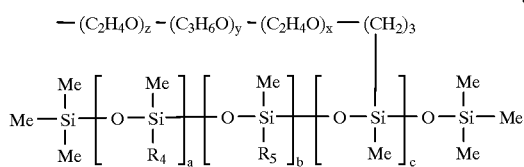

wherein in said formulae (I) and (V):
M_e represents a methyl radical;
$C_2H_4O$ represents a —CH₂—CH₂—O— group;
$C_3H_6O$ represents a —CH₂—CH(CH₃)—O group;
a represents an integer ranging from 0 to 200;
b represents an integer ranging from 0 to 200;
c represents an integer ranging from 1 to 200;
R₄ represents a —(CH₂)ₙCH₃ or phenyl radical, wherein n represents an integer ranging from 0 to 10;
R₅ represents a —(CH₂)₃—(OCH₂CH₂)ₓ—(OCH₂CH(CH₃))ᵧ—(OCH₂CH₂)_z—OH radical, wherein x, y, and z independently represent an integer ranging from 0 to 20;
d and e independently range from 1 to 2, wherein d+e=3; and
M is selected from H, Na, K, Li, NH₄, and N(CH₂CH₂OH)₃.

4. A method according to claim 2, wherein said at least one silicone surfactant contains a phosphate group and is selected from compounds of formula (II):

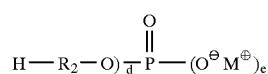

wherein

R₂ represents a radical of formula (VI):

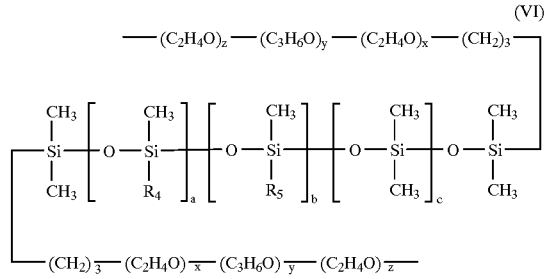

wherein in said formulae (II) and (VI):
M_e represents a methyl radical;
$C_2H_4O$ represents a —CH₂—CH₂—O— group;
$C_3H_6O$ represents a —CH₂—CH(CH₃)—O group;
a represents an integer ranging from 0 to 200;
b represents an integer ranging from 0 to 200;
c represents an integer ranging from 1 to 200;
R₄ represents a —(CH₂)ₙCH₃ or phenyl radical, wherein n represents an integer ranging from 0 to 10;
R₅ represents a —(CH₂)₃—(OCH₂CH₂)ₓ—(OCH₂CH(CH₃))ᵧ—(OCH₂CH₂)_z—OH radical, wherein x, y, and z independently represent an integer ranging from 0 to 20;
d and e independently range from 1 to 2, wherein d+e=3; and
M is selected from H, Na, K, Li, NH₄, and N(CH₂CH₂OH)₃.

5. A method according to claim 2, wherein said at least one silicone surfactant contains a phosphate group and is selected from compounds of formula (III):

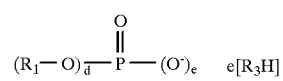

wherein

R₁ represents a radical of formula (V):

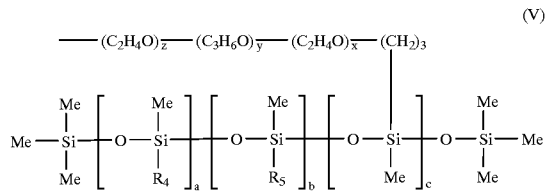

wherein in said formulae (III) and (V):
M_e represents a methyl radical;
$C_2H_4O$ represents a —CH₂—CH₂—O— group;
$C_3H_6O$ represents a —CH₂—CH(CH₃)—O group;
a represents an integer ranging from 0 to 200;
b represents an integer ranging from 0 to 200;
c represents an integer ranging from 1 to 200;
R₄ represents a —(CH₂)ₙCH₃ or phenyl radical, wherein n represents an integer ranging from 0 to 10;
R₅ represents a —(CH₂)₃—(OCH₂CH₂)ₓ—(OCH₂CH(CH₃))ᵧ—(OCH₂CH₂)_z—OH radical, wherein x, y, and z independently represent an integer ranging from 0 to 20;
d and e independently range from 1 to 2, wherein d+e=3;
R₃ is selected from:

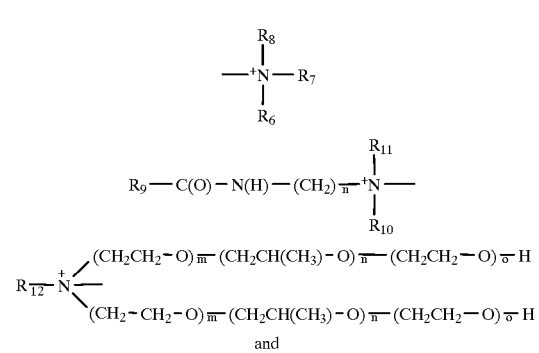

and

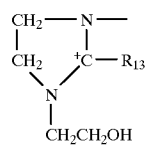

wherein $R_6$–$R_9$ independently represent an alkyl radical having from 1 to 20 carbon atoms;

$R_{10}$ and $R_{11}$ independently represent an alkyl radical having from 1 to 3 carbon atoms;

$R_{12}$ and $R_{13}$ independently represent an alkyl radical having from 6 to 20 carbon atoms; and m, n, and o independently represent an integer ranging from 0 to 20.

6. A method according to claim 2, wherein said at least one silicone surfactant contains a phosphate group and is selected from compounds of formula (IV):

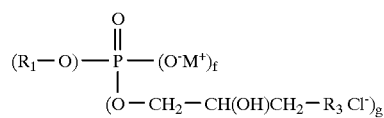

wherein $R_1$ represents a radical of formula (V):

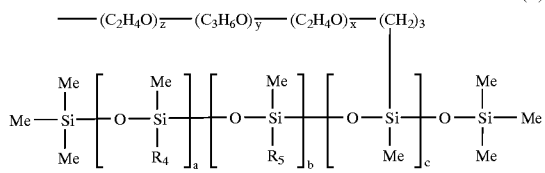

wherein in said formula (IV) and (V):

$M_e$ represents a methyl radical;

$C_2H_4O$ represents a —$CH_2$—$CH_2$—O— group;

$C_3H_6O$ represents a —$CH_2$—$CH(CH_3)$—O group;

a represents an integer ranging from 0 to 200;

b represents an integer ranging from 0 to 200;

c represents an integer ranging from 1 to 200;

$R_4$ represents a —$(CH_2)_n CH_3$ or phenyl radical, wherein n represents an integer ranging from 0 to 10;

$R_5$ represents a —$(CH_2)_3$—$(OCH_2CH_2)_x$—$(OCH_2CH(CH_3))_y$—$(OCH_2CH_2)_z$—OH radical, wherein x, y, and z independently represent an integer ranging from 0 to 20;

f represents 0 or 1, g represents 1 or 2, wherein f+g=2;

$R_3$ is selected from

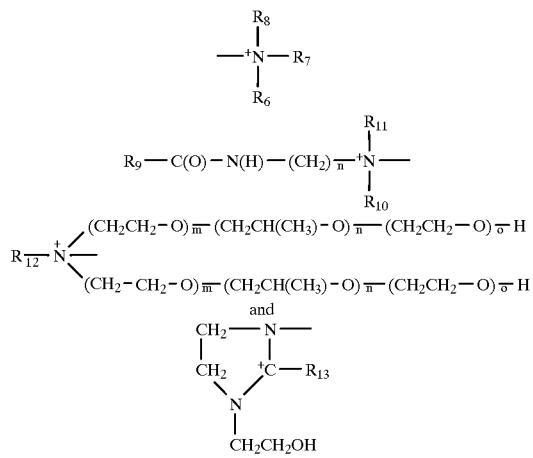

wherein $R_6$–$R_9$ independently represent an alkyl radical having from 1 to 20 carbon atoms;

$R_{10}$ and $R_{11}$ independently represent an alkyl radical having from 1 to 3 carbon atoms;

$R_{12}$ and $R_{13}$ independently represent an alkyl radical having from 6 to 20 carbon atoms; and m, n, and o independently represent an integer ranging from 0 to 20.

7. A method according to claim 2, wherein said at least one silicone surfactant contains a sulphate group and is selected from compounds of formula (VII):

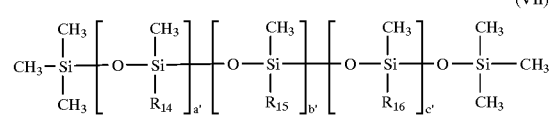

wherein:

$R_{14}$ represents an alkyl radical having from 1 to 8 carbon atoms or a phenyl radical;

$R_{15}$ represents a —$(CH_2)_3$—O—$(CH_2CH_2O)_u$—$(CH_2CH(CH_3)$ —O$)_v$—$(CH_2CH_2O)_w$—$SO_3^-M^+$ radical, wherein M is selected from Na, K, Li, and $NH_4$, and u, v, and w independently represent an integer ranging from 0 to 100;

$R_{16}$ represents a —$(CH_2)_3$—O—$(CH_2CH_2O)_u$—$(CH_2CH(CH_3)$—O$)_v$—$(CH_2CH_2O)$—H radical, wherein u, v, and w independently represent an integer ranging from 0 to 100;

a' and c' independently represent an integer ranging from 0 to 50; and b' represents an integer ranging from 1 to 50.

8. A method according to claim 2, wherein said at least one silicone surfactant contains a sulphonate group and is obtained by reacting a silicone of formula (VIII):

$$A-\underset{\underset{CH_3}{|}}{\overset{\overset{CH_3}{|}}{Si}}-O-\left[\underset{\underset{CH_3}{|}}{\overset{\overset{CH_3}{|}}{Si}}-O\right]_i-\left[\underset{\underset{Q-COOH}{|}}{\overset{\overset{CH_3}{|}}{Si}}-O\right]_j-\underset{\underset{CH_3}{|}}{\overset{\overset{CH_3}{|}}{Si}}-A \quad (VIII)$$

wherein:
Q represents $(CH_2)_r$, wherein r represents an integer ranging from 3 to 17;
j represents an integer ranging from 1 to 10 and A represents a methyl radical, or j represents 0 and A represents a —Q—COOH radical; and
I represents an integer ranging from 1 to 200; with a taurine derivative of formula $R_{17}$—NH—$(CH_2)_2$—$SO_3M$, wherein $R_{17}$ represents an alkyl radical having from 1 to 40 carbon atoms and M is selected from Na, K, Li, and $NH_4$.

9. A method according to claim 2, wherein said at least one silicone surfactant contains a sulphonate group and is selected from compounds of formula (IX):

$$R_{\overline{18}}-\underset{\underset{R_1}{|}}{\overset{\overset{R_1}{\oplus}}{N}}-(CH_2)_{\overline{2}}-SO_3M'Cl^- \quad (IX)$$

wherein:
$R_{18}$ represents an alkyl radical having from 1 to 40 carbon atoms;
$R_1$ represents a radical of formula (V):

$$\begin{array}{c} -(C_2H_4O)_{\overline{z}}-(C_3H_6O)_{\overline{y}}-(C_2H_4O)_{\overline{x}}-(CH_2)_3 \\ | \\ Me-\underset{\underset{Me}{|}}{\overset{\overset{Me}{|}}{Si}}-\left[O-\underset{\underset{R_4}{|}}{\overset{\overset{Me}{|}}{Si}}\right]_a-\left[O-\underset{\underset{R_5}{|}}{\overset{\overset{Me}{|}}{Si}}\right]_b-\left[O-\underset{\underset{Me}{|}}{\overset{\overset{Me}{|}}{Si}}\right]_c-O-\underset{\underset{Me}{|}}{\overset{\overset{Me}{|}}{Si}}-Me \end{array} \quad (V)$$

wherein in formulae (IX) and (V):
$M_e$ represents a methyl radical;
$C_2H_4O$ represents a —$CH_2$—$CH_2$—O— group;
$C_3H_6O$ represents a —$CH_2$—$CH(CH_3)$—O group;
a represents an integer ranging from 0 to 200;
b represents an integer ranging from 0 to 200;
c represents an integer ranging from 1 to 200;
$R_4$ represents a —$(CH_2)_n$ $CH_3$ or phenyl radical, wherein n represents an integer ranging from 0 to 10;
$R_5$ represents a —$(CH_2)_3$—$(OCH_2CH_2)_x$—$(OCH_2CH(CH_3))_y$—$(OCH_2CH_2)_z$—OH radical, wherein x, y, and z independently represent an integer ranging from 0 to 20; and
M' is selected from Na, K, Li, and $NH_4$.

10. A method according to claim 1, wherein said at least one oil is present in an amount of at least 65% by weight relative to the total weight of said fatty phase.

11. A method according to claim 1, wherein said at least one oil is selected from volatile hydrocarbon oils, volatile silicone oils, or mixtures thereof.

12. A method according to claim 11, wherein said at least one oil is selected from isoparaffins, volatile cyclic silicones having from 3 to 8 silicon atoms, dimethylsiloxane/methylalkylsiloxane-type cyclocopolymers, volatile linear silicones having from 2 to 9 silicon atoms, or mixtures thereof.

13. A method according to claim 12, wherein said volatile cyclic silicones have from 4 to 6 silicon atoms.

14. A method according to claim 11, wherein said at least one oil is selected from isododecane, cyclotetradimethylsiloxane, cyclopentadimethylsiloxane, cyclohexadimethylsiloxane, dimethylsiloxane/methyloctylsiloxane cyclocopolymer, hexamethyidisiloxane, hexylheptamethyltrisiloxane, octylheptamethyltrisiloxane, or mixtures thereof.

15. A method according to claim 1, wherein said poly ($C_1$–$C_{20}$)alkylsiloxanes have a viscosity at 25° C. of no greater than 0.06 m²/s.

16. A method according to claim 1, wherein said poly ($C_1$–$C_{20}$)alkylsiloxanes are selected from alkylmethylpolysiloxanes, linear polydimethylsiloxanes, or mixtures thereof.

17. A method according to claim 1, wherein said fatty phase additionally comprises at least one other fatty substance in addition to said at least one oil, said at least one other fatty substance being present in an amount of no greater than 7% by weight relative to the total weight of said emulsion.

18. A method according to claim 17, wherein said fatty phase comprises from 65% to 98% of said at least one oil and from 2% to 35% of said at least one other fatty substance, by weight relative to the total weight of said fatty phase.

19. A method according to claim 17, wherein said at least one other fatty substance is selected from vegetable oils, mineral oils, animal oils, synthetic oils, pasty fatty substances, gums, or waxes.

20. A method according to claim 10, wherein said at least one oil is present in said fatty phase in an amount of at least 75% by weight, relative to the total weight of said fatty phase.

21. A method according to claim 20, wherein said at least one oil is present in said fatty phase in an amount of 100% by weight, relative to the total weight of said fatty phase.

22. A method according to claim 1, wherein said emulsion comprises from 5–40% by weight of said fatty phase, from 0.5–15% by weight of said at least one silicone surfactant comprising at least one anionic group, and from 15–94.5% by weight of said aqueous phase, relative to the total weight of the emulsion.

23. A method according to claim 22, wherein said emulsion comprises from 12–30% by weight of said fatty phase, from 3–6% by weight of said at least one silicone surfactant comprising at least one anionic group, and from 40–70% by weight of said aqueous phase, relative to the total weight of the emulsion.

24. A method according to claim 1, wherein said emulsion is present in a cosmetic, pharmaceutical, or hygienic composition.

25. A method according to claim 24, wherein said composition is in the form of a make-up product, a skin-care product or an anti-sun product.

26. A method according to claim 25, wherein said make-up product is in the form of a foundation, blusher, eyeshadow, eyeliner, mascara, or lipstick; said skin-care product is in the form of a cream, milk, or serum; and said anti-sun product is in the form of a cream, milk or serum.

27. An oil-in-water emulsion comprising:
(a) an aqueous phase;

(b) a fatty phase comprising at least one oil selected from volatile oils and poly($C_1$–$C_{20}$)alkylsiloxanes, said at least one oil being present in an amount of at least 65% by weight relative to the total weight of the fatty phase;

(c) at least one silicone surfactant comprising at least one anionic group selected from:

(i) silicone surfactants containing a phosphate group selected from formulae (I), (II), (III), and (IV):

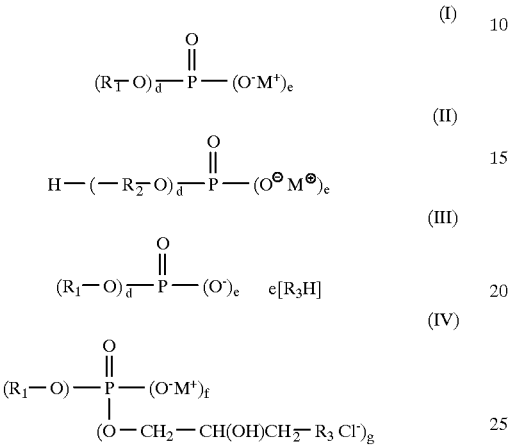

wherein
$R_1$ represents a radical of formula (V):

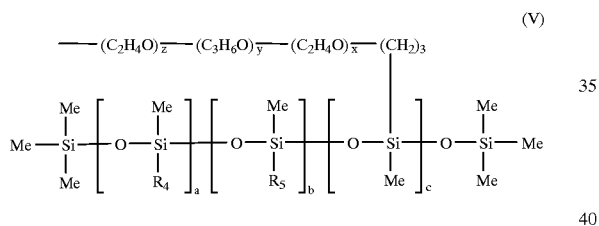

$R_2$ represents a radical of formula (VI):

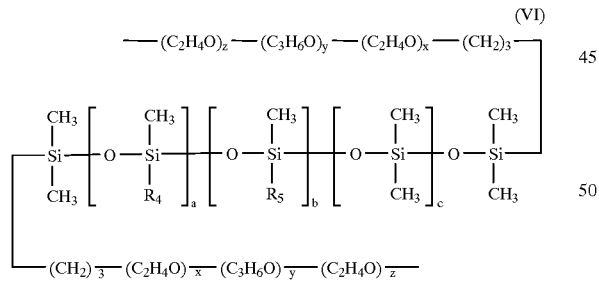

wherein in said formulae (V) and (VI):
$M_e$ represents a methyl radical;
$C_2H_4O$ represents a —$CH_2$—$CH_2$—O— group;
$C_3H_6O$ represents a —$CH_2$—$CH(CH_3)$—O group;
a represents an integer ranging from 0 to 200;
b represents an integer ranging from 0 to 200;
c represents an integer ranging from 1 to 200;
$R_4$ represents a —$(CH_2)_nCH_3$ or phenyl radical, wherein n represents an integer ranging from 0 to 10;
$R_5$ represents a —$(CH_2)_3$—$(OCH_2CH_2)_x$—$(OCH_2CH(CH_3))_y$—$(OCH_2CH_2)_z$—OH radical, wherein x, y, and z independently represent an integer ranging from 0 to 20;

$R_3$ is selected from:

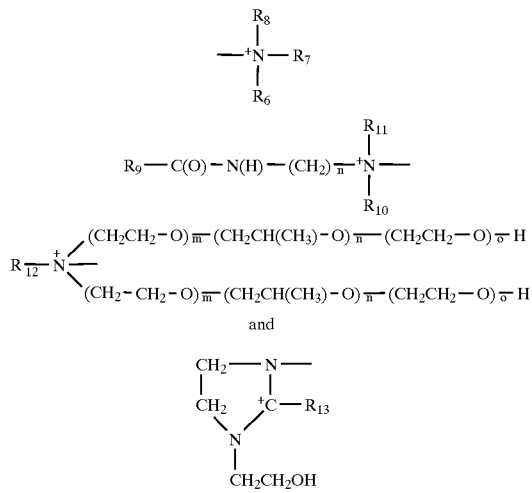

wherein
$R_6$–$R_9$ independently represent an alkyl radical having from 1 to 20 carbon atoms;
$R_{10}$ and $R_{11}$ independently represent an alkyl radical having from 1 to 3 carbon atoms;
$R_{12}$ and $R_{13}$ independently represent an alkyl radical having from 6 to 20 carbon atoms;
m, n, and o independently represent an integer ranging from 0 to 20;
d and e independently range from 1 to 2, wherein d+e=3;
f is equal to 0 or 1 and g is equal to 1 or 2, wherein f+g=2; and
M is selected from H, Na, K, Li, $NH_4$ and $N(CH_2CH_2OH)_3$;

(ii) silicone surfactants containing a sulphate group of formula (VII)

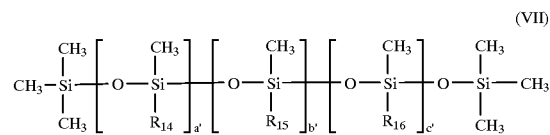

wherein
$R_{14}$ represents an alkyl radical having from 1 to 8 carbon atoms or a phenyl radical;
$R_{15}$ represents a —$(CH_2)_3$—O—$(CH_2CH_2O)_u$—$(CH_2CH(CH_3)$—O$)_v$—$(CH_2CH_2O)_w$—$SO_2^-M^+$ radical, wherein M is selected from Na, K, Li, and $NH_4$ and u, v, and w independently represent an integer ranging from 0 to 100;
$R_{16}$ represents a —$(CH_2)_3$—O—$(CH_2CH_2O)_u$—$(CH_2CH(CH_3)$—O$)_v$—$(CH_2CH_2O)_w$—H radical, wherein u, v, and w independently represent an integer ranging from 0 to 100;
a' and c' independently represent an integer ranging from 0 to 50; and
b' represents an integer ranging from 1 to 50;

(iii) silicone surfactants containing a sulphonate group obtained by reacting a silicone of formula (VIII):

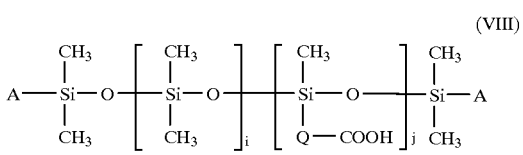

wherein:

Q represents $(CH_2)_r$, wherein r represents an integer ranging from 3 to 17;

j represents an integer ranging from 1 to 10 and A represents a methyl radical, or j represents 0 and A represents a —Q—COOH radical; and I represents an integer ranging from 1 to 200; with a taurine derivative of formula $R_{17}$—NH—$(CH_2)_2$—$SO_3M'$, wherein $R_{17}$ represents an alkyl radical having from I to 40 carbon atoms and M' is selected from Na, K, Li, and $NH_4$; and (iv) silicone surfactants containing a sulphonate group of formula (IX):

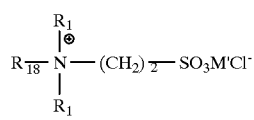

wherein $R_{18}$ represents an alkyl radical having from 1 to 40 carbon atoms;

$R_1$ represents a radical of formula (V) as defined in formula (I); and

M' is selected from Na, K, Li, and $NH_4$; said at least one silicone surfactant and said fatty phase being present in the emulsion in an amount sufficient to decrease the transfer and/or migration of or to improve the persistence and/or behavior of said emulsion on the skin and wherein when said at least one silicone surfactant comprising at least one anionic group is a silicone surfactant of formula (I), said fatty phase of said emulsion comprises at least one fatty substance other than said at least one oil in an amount of no greater than 7% by weight relative to the total weight of said emulsion.

28. An oil-in-water emulsion according to claim 27, wherein said at least one oil is selected from volatile hydrocarbon oils or volatile silicone oils.

29. An oil-in-water emulsion according to claim 27, wherein said at least one oil is selected from isoparaffins, volatile cyclic silicones having from 3 to 8 silicon atoms, dimethylsiloxane/methylalkylsiloxane-type cyclocopolymers, volatile linear silicones having from 2 to 9 silicon atoms, or mixtures thereof.

30. An oil-in-water emulsion according to claim 29, wherein said volatile cyclic silicones have from 4 to 6 silicon atoms.

31. An oil-in-water emulsion according to claim 27, wherein said at least one oil is selected from isododecane, cyclotetradimethylsiloxane, cyclopentadimethylsiloxane, cyclohexadimethylsiloxane, dimethylsiloxane/methyloctylsiloxane cyclocopolymer, hexamethyldisiloxane, hexylheptamethyltrisiloxane, octylheptamethyltrisiloxane, or mixtures thereof.

32. An oil-in-water emulsion according to claim 27, wherein said poly $(C_1-C_{20})$alkylsiloxanes have a viscosity at 25° C. of no greater than 0.06 m²/s.

33. An oil-in-water emulsion according to claim 27, wherein said poly $(C_1-C_{20})$alkylsiloxanes are selected from alkylmethylpolysiloxanes, linear polydimethylsiloxanes, or their mixtures.

34. An oil-in-water emulsion according to claim 27, wherein said at least one oil is present in said fatty phase in an amount of at least 75% by weight, relative to the total weight of said fatty phase.

35. An oil-in-water emulsion according to claim 34, wherein said at least one oil is present in said fatty phase in an amount of 100% by weight, relative to the total weight of said fatty phase, and said at least one silicone surfactant is of a formula other than formula (I).

36. An oil-in-water emulsion according to claim 27, wherein said fatty phase additionally comprises at least one other fatty substance in an amount no greater than 7% by weight relative to the total weight of said emulsion.

37. An oil-in-water emulsion according to claim 36, wherein said at least one other fatty substance is selected from vegetable oils, mineral oils, animal oils, synthetic oils, pasty fatty substances, gums, or waxes.

38. An oil-in-water emulsion according to claim 27, wherein said oil-in-water emulsion comprises from 5–40% by weight of said fatty phase, from 0.5–15% by weight of said at least one silicone surfactant comprising at least one anionic group, and from 15–94.5% by weight of said aqueous phase, relative to the total weight of said oil-in-water emulsion.

39. An oil-in-water emulsion according to claim 38, wherein said oil-in-water emulsion comprises from 12–30% by weight of said fatty phase, from 3–6% by weight of said at least one silicone surfactant comprising at least one anionic group, and from 40–70% by weight of said aqueous phase, relative to the total weight of said oil-in-water emulsion.

40. An oil-in-water emulsion according to claim 27, wherein said oil-in-water emulsion is present in a cosmetic, pharmaceutical, or hygienic composition.

41. A composition according to claim 40, wherein said composition is in the form of a make-up product, a skin-care product or an anti-sun product.

42. A composition according to claim 41, wherein said make-up product is in the form of a foundation, blusher, eyeshadow, eyeliner, mascara, or lipstick; said skin-care product is in the form of a cream, milk, or serum; and said anti-sun product is in the form of a cream, milk or serum.

43. A method for the non-therapeutic treatment of the skin or scalp, said method comprising the step of applying to said skin or scalp an effective amount of an oil-in-water emulsion according to claim 27.

44. A method for the non-therapeutic treatment of the skin or scalp comprising the step of applying to said skin or scalp an effective amount of a cosmetic, pharmaceutical, or hygienic composition according to claim 40.

45. A method for the making up the skin or scalp comprising the step of applying to said skin or scalp an effective amount of an oil-in-water emulsion according to claim 27.

46. A method for the making up the skin and/or scalp comprising the step of applying to said skin or scalp an effective amount of a composition according to claim 40.

* * * * *

UNITED STATES PATENT AND TRADEMARK OFFICE
CERTIFICATE OF CORRECTION

PATENT NO. : 5,922,311
DATED : July 13, 1999
INVENTOR(S) : Nadia TERREN and Sophie FAVRE It is certified that error appears in the above-indentified patent and that said Letters Patent is hereby corrected as shown below:

IN THE CLAIMS:

Claim 1, col. 12, line 55, "$(C_{1-C20})$" should read --$(C_1-C_{20})$--.

Claim 4, col. 13, line 43, in formula (II), after "H----", insert --(- --.

Claim 27, col. 21, line 18, "I" should read --1--.

Signed and Sealed this

Twenty-third Day of November, 1999

Q. TODD DICKINSON

Attest:

Attesting Officer        Acting Commissioner of Patents and Trademarks